(12) United States Patent
Greenwald et al.

(10) Patent No.: US 10,217,526 B2
(45) Date of Patent: *Feb. 26, 2019

(54) METHOD FOR MEASURING STRENGTH OF ASSOCIATIONS

(75) Inventors: Anthony G. Greenwald, Seattle, WA (US); N. Sriram, Charlottesville, VA (US)

(73) Assignee: University of Washington, Seattle, WA (US)

( * ) Notice: Subject to any disclaimer, the term of this patent is extended or adjusted under 35 U.S.C. 154(b) by 2765 days.

This patent is subject to a terminal disclaimer.

(21) Appl. No.: 11/455,493

(22) Filed: Jun. 19, 2006

(65) Prior Publication Data

US 2006/0287991 A1    Dec. 21, 2006

Related U.S. Application Data

(60) Provisional application No. 60/691,488, filed on Jun. 17, 2005.

(51) Int. Cl.
    *G09B 7/00*      (2006.01)
    *G16H 10/20*     (2018.01)
    *A61B 5/16*      (2006.01)

(52) U.S. Cl.
    CPC .......... *G16H 10/20* (2018.01); *A61B 5/167* (2013.01); *G09B 7/00* (2013.01)

(58) Field of Classification Search
    CPC .. A61B 5/16; A61B 5/167; G09B 7/00; G09B 7/06

(Continued)

(56) References Cited

U.S. PATENT DOCUMENTS 4,627,818 A * 12/1986 Von Fellenberg ............ 434/236
2006/0286519 A1 * 12/2006 Burnham et al. ............. 434/236

OTHER PUBLICATIONS

Greenwald et al., "Measuring Individual Differences in Implicit Cognition: The Implicit Association Test," Journal of Personality and Social Psychology, 74 (6), 1464-1480 (1998).

(Continued)

*Primary Examiner* — Peter Egloff
(74) *Attorney, Agent, or Firm* — Sunstein Kann Murphy & Timbers LLP

(57) ABSTRACT

An improved method of measuring a subject's strength of associations involving each of a first pair of first and second categories with each of a second pair of third and fourth categories includes having the subject respond to a first set of trials in a first manner when there is presented an exemplar of either the first category or the third category and in a second manner when there is presented an exemplar of either the second category or the fourth category and presenting the subject with a first series of exemplars in the first set of trials, the first series including exemplars in all four categories. The method further includes having the subject respond to a second set of trials in one of the two manners when there is presented the exemplar of either the second category or the third category and in the other of the two manners when there is presented the exemplar of either the first category or the fourth category and presenting the subject with a second series of exemplars in the second set of trials, the second series including exemplars in all four categories. Latency is measured in each trial from time of exemplar presentation to the subject to a response by the subject to produce latency measurements. A measure is calculated of the subject's strength of associations involving each of the first and second categories with each of the third and fourth categories from the latency measurements.

13 Claims, 5 Drawing Sheets

(58) Field of Classification Search
USPC .................................................. 434/236, 323
See application file for complete search history.

(56) References Cited

OTHER PUBLICATIONS

Greenwald et al., "Health of the Implicit Association Test at Age 3," Zeitschrift für Experimentelle Psychologie, 48 (2), 85-93 (2001).

Nosek et al., "The Implicit Association Test at Age 7: A Methodological and Conceptual Review," In J. A. Bargh (Ed.), Automatic processes in social thinking and behavior. Psychology Press. 265-292 (no date available).

Greenwald et al., "Understanding and Using the Implicit Association Test: I. An Improved Scoring Algorithm," Journal of Personality and Social Psychology, 85 (2), 197-216 (2003).

Nosek et al., "Understanding and Using the Implicit Association Test: II. Method Variables and Construct Validity," Personality and Social Psychology Bulletin, 31 (2), 166-180 (2005).

Poehlman et al., "Understanding and Using the Implicit Association Test: III. Meta-analysis of Predictive Validity" 1-75 (no date available).

Bosson et al., "Stalking the Perfect Measure of Implicit Self-Esteem: The Blind Men and the Elephant Revisited?" Journal of Personality and Social Psychology, 79 (4), 631-643 (2000).

Furnham et al., "The Relationship Between the Revised NEO-Personality Inventory and the Myers-Briggs Type Indicator," Social Behavior and Personality, 31 (6), 577-584 (2003).

Steffens et al., "Predicting Spontaneous Big-Five Behavior with Implicit Association Tests," European Journal of Psychological Assessment (no date available).

McCrae et al. "Reinterpreting the Myers-Briggs Type Indicator from the Perspective of the Five-Factor Model of Personality," Journal of Personality, 57 (1), 17-40 (1989).

Kopelman et al., "The Study of Values: Construction of the fourth edition," Journal of Vocational Behavior, 62, 203-220 (2003).

Greenwald et al., "Using the Implicit Association Test to Measure Self-Esteem and Self-Concept" Journal of Personality and Social Psychology, 79 (6), 1022-1038(2000).

Rudman et al., "Implicit Self-Concept and Evaluative Implicit Gender Stereotypes: Self and Ingroup Share Desirable Traits" Personality and Social Psychology Bulletin, 27 (9), 1164-1178 (2001).

* cited by examiner

| Structure of Standard IAT (Flower-Insect Implicit Attitude Measure) | | | | |
|---|---|---|---|---|
| Block | no. of trials | Function | Instructions for left key: Press for | Instructions for right key: Press for |
| 1 | 20 | target concept practice | flower names | insect names |
| 2 | 20 | attribute practice | unpleasant words | pleasant words |
| 3 | 20 | first combined task practice | flower names OR unpleasant words | insect names OR pleasant words |
| 4 | 40 | first combined task test | flower names OR unpleasant words | insect names OR pleasant words |
| 5 | 40 | target concept reversal practice | insect names | flower names |
| 6 | 20 | second combined task practice | insect names OR unpleasant words | flower names OR pleasant words |
| 7 | 40 | second combined task test | insect names OR unpleasant words | flower names OR pleasant words |
| Total | 200 | | | |

FIG. 1

(PRIOR ART)

| Structure of Improved IAT (Flower-Insect Implicit Attitude Measure) ||||| 
|---|---|---|---|---|
| Block | No. of trials | Function | General instruction for left key: "Press for anything else" [items are shown in brackets] | Instruction for right key |
| 1 | 20 to 24 | first combined task | [flower names or unpleasant words] | press for insect names OR pleasant words |
| 2 | 20 to 24 | second combined task | [insect names or unpleasant words] | press for flower names OR pleasant words |
| 3 | 20 to 24 | Repeat Block 1 [alternately, repeat Block 2] |||
| 4 | 20 to 24 | Repeat Block 2 [alternately, repeat Block 1] |||
| Total | 80–96 | ||||

Trials 1–4 in each block may be limited to the two target concepts — in this example, these would be insect names and flower names.

FIG. 3

SLAT for Brand Personality: Illustration with PC/Windows vs. Apple/Mac

101. Type I: imaginative, elite, streamlined, graphic, sexy
102. Type O: ordinary, solid, square, textual, bland
103. PC/Windows: visual images associated with IBM, PC, Windows
104. Apple/Mac: visual images associated with Apple, Mac, OSX

FIG. 4

SLAT for Assessing Stereotype: Illustration with Asian Stereotype

201. Type AA: shy, diligent, study, small, light
202. Type NA: pushy, vacation, play, large, tall
203. Asian: Asia, China, Japan, Hong Kong, Korea
204. North American: Canada, Mexico, Alaska, USA, Toronto, Kansas

FIG. 5

IAT for Assessing Cigarette–Health Association Strengths (no higher-level representations involved)

301. Health:healthy, well, sound, vital
302. Illness: ill, sick, disease, hospital
303. Cigarettes: pictures of scenes with cigarettes
304. No cigarettes: pictures of (identical) scenes without cigarettes

FIG. 6

SLAT for Proposition–Category Associations (health and illness categories from FIG. 6 replaced with
propositional groupings of healthy vs. unhealthy behavior)

401. Type H: exercise more, eat less, lose weight, ride bicycle, low calorie
402. Type U: exercise less, eat more, gain weight, drive car, high calorie
403. Cigarettes: pictures of scenes with cigarettes
404. No cigarettes: pictures of (identical) scenes without cigarettes

FIG. 7

SLAT for Proposition–Proposition Associations (cigarette category from FIG. 7 replaced with propositional representation of smoking behavior)

501. Type H: exercise more, eat less, lose weight, ride bicycle, low calorie
502. Type U: exercise less, eat more, gain weight, drive car, high calorie
503. Type S: light up, inhale smoke, exhale smoke, find ashtray
504. Type NS: no smoking, smoke detector, no ashtrays, indoor air quality

FIG. 8

METHOD FOR MEASURING STRENGTH OF ASSOCIATIONS

CROSS-REFERENCE TO RELATED APPLICATIONS

This patent application claims priority under 35 U.S.C. § 119(e) to U.S. Provisional Patent Application No. 60/691,488 filed Jun. 17, 2005, entitled IMPLICIT METHODS FOR MEASURING STRENGTHS OF ASSOCIATIONS, the disclosure of which is incorporated by reference herein in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of grant No. MH57672 awarded by the National Institute of Mental Health.

FIELD OF THE INVENTION

The invention generally relates to methods for measuring strengths of associations and, more particularly, the invention relates to an improved method of measuring the strength of association.

BACKGROUND OF THE INVENTION

Psychologists understand that people may not say what is on their minds either because they are unwilling or unable to do so. For example, a smoker when asked how much he or she smokes a day, may report smoking only two packs a day although the smoker actually smokes four packs a day. This may be because the smoker is embarrassed to admit the correct number of packs. This is an example of being unwilling to report a known answer. However, the smoker may report smoking only two packs a day because that is the amount the smoker honestly believes is consumed per day. This is an example of unknowingly giving an incorrect answer, also sometimes called self-deception. This example illustrates being unable to give the desired answer. The unwilling-unable distinction is like the difference between purposely hiding something from others and unconsciously hiding something from yourself. Many studies investigating psychological issues examine the thoughts and feelings that exist either outside of conscious awareness or outside of conscious control. Understanding the conscious-unconscious divergences is important to scientific psychology.

SUMMARY OF THE INVENTION

In one embodiment, the present invention provides an improved method of measuring a subject's strength of associations involving each of a first pair of first and second categories with each of a second pair of third and fourth categories. This embodiment includes having the subject respond to a first set of trials in a first manner when there is presented an exemplar of either the first category or the third category and in a second manner when there is presented an exemplar of either the second category or the fourth category. In the first set of trials, the method includes presenting the subject with a first series of exemplars that are in all four categories. The method also includes having the subject respond to a second set of trials in one of the two manners when there is presented an exemplar of either the second category or the third category and in the other of the two manners when there is presented the exemplar of either the first category or the fourth category. Also, in the second set of trials, the method includes presenting the subject with a second series of exemplars. The second series includes exemplars in all four categories. This embodiment also includes measuring latency in each trial from time of exemplar presentation to the subject to a response by the subject to produce latency measurements. The embodiment finally includes calculating a measure of the subject's strength of associations involving each of the first and second categories with each of the third and fourth categories from the latency measurements.

In a further related embodiment, the trials of each set may alternate between presenting the subject with an arbitrary exemplar in one of the first pair of categories with an arbitrary exemplar in one of the second pair of categories.

Alternatively or in addition, calculating a measure may include calculating a difference between a mean latency for the first set of trials and a mean latency for the second set of trials and dividing the difference by a standard deviation of latency measurements for the first and the second set of trials.

In further related embodiments, the subject may be presented with fewer than 100 trials or the subject may be presented with fewer than 50 trials.

Alternatively or in addition, the first pair of categories may include an attribute and an opposing attribute. In further related embodiments, the first pair of categories may include a pleasant valence category and an opposed unpleasant valence category, and the method may measure the subject's strength of associations involving attitude. The first pair of categories may include human group categories and the second pair of categories may include trait categories, and the method may measure the subject's strength of associations involving stereotypes. The first pair of categories may include a self-referring category and an other-referring category, and the method may measure the subject's strength of associations involving identity.

In a further related embodiment, having the subject respond to the first set of trials and to the second set of trials may include providing instructions to the subject. The instructions may be to respond in one of the two manners to the exemplars of one of the first pair of categories or one of the second pair of categories, and to respond in the other of the two manners to the exemplars of any categories not thus instructed for the first manner of responding.

In a further related embodiment, the subject may not be required to respond to any trials other than those trials recited.

In related embodiments, the method may further include repeating the first set of trials with a third series of exemplars and repeating the second set of trials with a fourth series of exemplars. The subject may not be required to respond to any trials other than those trials recited.

In a further related embodiment, measuring latency in each trial may include measuring from the time of exemplar presentation to the subject to a correct response by the subject.

BRIEF DESCRIPTION OF THE DRAWINGS

The foregoing and advantages of the invention will be appreciated more fully from the following further description thereof with reference to the accompanying drawings wherein:

FIG. 1 shows a standard IAT procedure consisting of 200 trials;

FIG. 3 shows an improved IAT procedure according to an embodiment of the present invention;

FIG. 4 shows an exemplary SLAT for brand personality according to an embodiment of the present invention;

FIG. 5 shows an exemplary SLAT for assessing stereotype according to an embodiment of the present invention;

FIG. 6 shows an exemplary IAT for assessing cigarette-health association strengths according to an embodiment of the present invention;

FIG. 7 shows an exemplary SLAT for proposition-category associations according to an embodiment of the present invention; and FIG. 8 shows an exemplary SLAT for proposition-proposition associations according to an embodiment of the present invention.

DESCRIPTION OF ILLUSTRATIVE EMBODIMENTS

Figure 2:
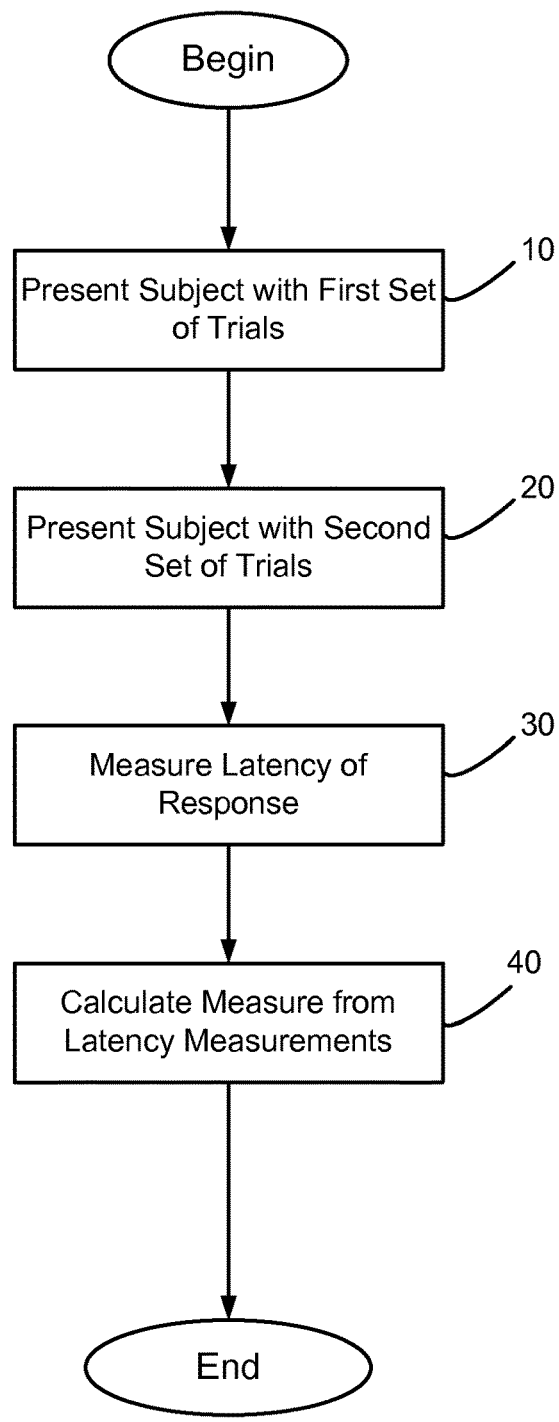
FIG. 2 shows a method of measuring a subject's strength of associations according to an embodiment of the present invention.

An Implicit Association Test (IAT) measures the implicit attitudes and beliefs that people are either unwilling or unable to report. The IAT may be used for the purposes of measuring the most important constructs of social cognition, e.g., attitudes, stereotypes, self-concept, and/or self-esteem. A. G. Greenwald et al. discuss an IAT in "Measuring Individual Differences in Implicit Cognition: The Implicit Association Test," *Journal of Personality and Social Psychology*, 74, pp. 1464-1480 (1998), which is incorporated by reference herein in its entirety. In a standard IAT, a subject responds to a series of items that are classified into four categories, typically, two representing a concept discrimination such as flowers versus insects and two representing an attribute discrimination such as pleasant versus unpleasant valence. The established form of the IAT typically consists of seven blocks of trials, three of which require the test taker to rapidly classify items from two of the four categories, and another four blocks of trials that present items from all four categories as two "combined" tasks. For example, in Task A, subjects are asked to respond rapidly with a right-hand key press, such as the letter "i" with a right hand finger, to items representing one concept or one attribute (e.g., insects or unpleasant), and with a left-hand key press, such as the letter "e" with a left hand finger, to items from the remaining two categories (e.g., flowers or pleasant). Subjects then perform a second task, in Task B, in which the key assignments for one of the pairs is switched (such that flowers and unpleasant share a response, likewise insects and pleasant). For example, sample items for each category may be the following:

Flowers: rose, tulip, daisy, dahlia, orchid, daffodil
Insects: wasp, mosquito, roach, centipede, beetle, hornet
Pleasant: love, peace, cheer, friend, diamond, rainbow
Unpleasant: crash, grief, hatred, stink, vomit, agony The IAT produces measures derived from latencies of responses to these two tasks. These measures are interpreted in terms of association strengths by assuming that subjects respond more rapidly when the concept and attribute mapped onto the same response are strongly associated than when they are weakly associated. In this case, it is regularly observed that the response times for Task B responses average 250-300 msec or more slower than for Task A responses. This extremely large IAT effect has been interpreted theoretically as revealing that the strengths of associations involved in Task A responses, i.e., flower-pleasant and insect-unpleasant, are stronger than the strengths of associations involved in Task B responses, i.e., insect-pleasant and flower-unpleasant.

The measure is called implicit because it is inferred from performance rather than being the response to a question that asks the respondent to report the strengths of these associations. The latter would be called an explicit or self-report measure. Implicit measures are valuable because they have been shown to provide information useful in predicting some behaviors that are not predicted well by explicit measures. Implicit measures are especially useful in predicting behaviors in the domain of prejudices and stereotypes.

The seven blocks of trials used in the standard IAT typically involves a minimum of 180 trials. The most commonly used IAT procedure is shown in FIG. 1 consisting of 200 trials, which represents the standard IAT that is currently in research use.

Embodiments of the present invention provide an improved method of measuring the strength of associations for items in selected categories. The method may be administered in about one-third of the time presently required for the existing, standard IAT, while preserving the psychometric virtues of the standard IAT. Benefits include the IAT's effective measurement of association strengths and its ability to resist influence by self-presentation strategies, which makes it resistant to faking. In addition, the method may be used for all purposes for which the standard IAT is used.

FIG. 2 shows an improved method of measuring a subject's strength of associations according to an embodiment of the present invention. Similar to the standard IAT, the subject responds to a series of items that are classified into two pairs of four categories. The first pair may include the first and second categories and the second pair may include the third and fourth categories. However, unlike the standard IAT, the subjects are instructed to respond only to items or exemplars for the two categories associated with a right-hand key, and are instructed to give a left-hand response to "any other" presented items. In addition, the subject is not required to respond to blocks of single-task practice trials, e.g., corresponding to Blocks 1, 2, and 5 of the Standard IAT shown in FIG. 1. Thus, in step 10, the subject is presented with a first set of trials that includes a first series of items. The subject is instructed to respond in one manner, e.g., a right-hand key, when presented with an item or exemplar from either the first category or the third category and instructed to respond in another manner, e.g., a left-hand key, when presented with any other item, e.g., an item from either the second category or the fourth category. The first set of trials includes items from each of the four categories. Preferably, the trials alternate between presenting the subject with an exemplar arbitrarily selected from the first pair of categories with an exemplar arbitrarily selected from the second pair of categories.

In step 20, the subject is presented with a second set of trials that includes a second series of items. The subject is instructed to respond in one manner, e.g., a right-hand key, when presented with an item from either the second category or the third category and instructed to respond in another manner, e.g., a left-hand key, when presented with an item from either the first category or the fourth category. Like the first set of trials, the second set of trials includes items from each of the four categories. Again, preferably, the trials alternate between presenting the subject with an exemplar arbitrarily selected from the first pair of categories with an exemplar arbitrarily selected from the second pair of categories.

In step 30, the latency of the subject's response in each trial is measured from the time of the item's presentation to the subject until the time of the response by the subject. The latency measurements may be measured using a variety of methods well known to those in the art. For example, the test may be administered using a computer and display device. The latency may then be determined, e.g., using software on the computer, by measuring the delay in response from the time the item is presented to the subject on the display device until the time when the subject responds to the computer, e.g., via a keyboard. The computer may be connected over a network, e.g., the Internet, and the information may be sent to the computer from a server connected to the network. The latency measurements may be adjusted to take into account any delays associated with sending the information over the network from the server to the computer and, similarly, any delays in receiving the information sent from the computer to the server. The test may be administered without the subject using a computer, e.g., over a telephone or a written test. The latency may then be determined by measuring the time the subject takes to answer the questions for the first set of trials and the second set of trials. The latency of the subject's response may be measured for both correct and incorrect answers. Alternatively, the latency may be measured for only a subject's correct responses in each trial.

These latency measurements are then used to calculate a measure of the subject's strength of associations involving each of the first and second categories with each of the third and fourth categories (step 40). The measure may be calculated by subtracting the mean latency for the first set of trials with the mean latency for the second set of trials and dividing the result by a standard deviation for the latency measurements for the first and the second set of trials. Steps 10 and 20 may be repeated, although the order may vary or stay the same. For example, step 20 may be repeated before step 10 is repeated or step 10 may be repeated and then step 20. In this case, the latency measurements may be calculated by subtracting the mean latency for both of the first sets of trials with the mean latency for both of the second sets of trials and dividing the result by the standard deviation for the latency measurements for all four sets of trials.

Embodiments of the present invention may provide a measure of the psychological construct of attitude when one of the two pairs of categories consists of the opposed valence categories of pleasant (e.g., good, positive, etc.) and unpleasant (e.g., bad, negative, etc.). Embodiments may also provide a measure of the psychological construct of stereotype when one of the two pairs of categories are human group categories, such as male and female, and the other of the two pairs are trait categories, such as warm and strong, or scientific and artistic; or family-oriented and career-oriented. These trait categories do not necessarily need to be opposed. Embodiments may also provide a measure of the psychological construct of identity or self-concept when one of the two pairs of categories consists of both a self-referring category (e.g., self, me, us, etc.), and an other-referring category (e.g., other, they, them, etc.).

FIG. 3 shows an improved IAT structure accordingly to an embodiment of the present invention. As shown in FIG. 3 and previously discussed with regard to FIG. 2, embodiments of the present invention differ from the standard IAT shown in FIG. 1 in a number of ways. First, there are no blocks of single-task practice trials (omitting anything corresponding to Blocks 1, 2, and 5 of the Standard IAT). Second, there are simplified instructions for blocks with four categories of items. Third, two repetitions of the same entire procedure (e.g., first repetition in Blocks 1-2; second in Blocks 3-4) provide an internal reliability estimate. The standard procedure shown in FIG. 1 does not include an exact repetition of procedures to produce two exactly parallel measures. However, it is possible to subdivide the total group of trials in the standard procedure into one measure based on Blocks 3 and 6 and another based on Blocks 4 and 7 of FIG. 1, as discussed by A. G. Greenwald et al. in "Understanding and Using the Implicit Association Test: I. An Improved Scoring Algorithm," *Journal of Personality and Social Psychology*, 85, pp. 197-216 (2003), which is incorporated by reference herein in its entirety. Lastly, embodiments of the present invention permit an ultra-short variation consisting only of Blocks 1 and 2, for a total of 40-48 trials, less than 25% of the length of the standard IAT. Other embodiments permit a longer version having approximately 80-96 trials, less than 50% of the length of the standard IAT.

A series of experiments, as shown in the examples below, has confirmed that the improved IAT has psychometric properties comparable to those of the standard IAT, with no more than minimal reduction of internal consistency and predictive validity in known-groups designs.

The Second Level Association Test (SLAT) is a new procedure derived from the IAT. As previously described, the IAT measures strengths of associations among mental representations at the level of concepts or categories. Like the IAT, the SLAT measures strengths of mental representations, but the representations among which association strengths are measured by the SLAT are cognitively more complex than for the IAT. The SLAT's measure is constructed from classification latencies provided by a test taker who classifies items from four defined sets of items using just two responses. At least one, often two, and possibly all four of the item sets in the SLAT correspond to representations more complex than categories. The SLAT's measure is based on the theory that the test taker will respond faster when the two groupings assigned to the same response are associated with each other in a mental representation at a level higher than the category level.

Four of the following examples indicate use of the SLAT in measuring associations involving these more-complex-than-category mental representations: (a) "brand personalities" (FIG. 4), (b) ethnic stereotypes (FIG. 5), and (c) propositions associated with health (FIGS. 6 and 7).

The items grouped as Type I (101 in FIG. 4) do not share membership in a category. That is, no category label encompasses all of these items in the way that rose, tulip, daisy, dahlia, orchid, and daffodil are subsumed by the category flower. If the Type I items do have something in common, it may be due to their being interrelated in a more complex (multi-category) representation, for which the "brand personality" may be an appropriate identification. Three of the items (imaginative, elite, sexy) are human traits that have no close semantic relation to one another. The other two terms (streamlined, graphic) describe nonhuman objects. The items in Type O (102) similarly lack interrelation in terms of semantic categories, but may nevertheless themselves be linked in a higher-level brand personality organization. In contrast, the items included in the PC/Windows (103) and Apple/Mac (104) groupings are contained in categories represented by the two brand names. In this SLAT two of the four groupings (101 and 102) involve representations more complex than categories.

FIG. 6 similarly includes two groupings (Type AA and Type NA) that lack category interrelations, along with two groupings (Asian and North American) that are typical categories. Additional examples of the SLAT—ones potentially useful in assessing associations involving smoking and health—are presented in FIGS. 7 and 8. For comparison, FIG. 6 presents an IAT (with all items at the category level) that is also related to smoking and health.

In FIG. 7, Types H and U (with the exception of the last item in each grouping) are verb-containing propositional predicates (i.e., descriptions of action, but with sentence subject words [which might be "I" or "you"] left unstated). To the extent that these items are cognitively interrelated in complex representations, it will be possible for the SLAT to reveal variations in association between those higher level structures and the category of cigarettes. FIG. 8 further extends the use of complex representations in the SLAT, with all four groupings drawing on cognitive representations more complex than categories.

The tasks represented by FIGS. 4-8 all involve two tasks assigned to the test-taker. One task pairs one of the first two groupings (e.g., Type H, 401 in FIG. 7) with one of the second two (e.g., smoking, 403 in FIG. 7), requiring that the same response be given to all items in both groupings. Respondents are simultaneously instructed to give a different response to all items in the remaining two groups. The two responses are done, respectively, with the index fingers of each hand on a computer keyboard. Latency of response is recorded for each response. A second task uses the remaining possible pairings of one of the first two with one of the second two groupings. Performance is scored using the D scoring algorithm described by Greenwald, Nosek, and Banaji (2003). (However, the D algorithm is potentially replaceable by possibly superior scoring systems that may be developed in the future.)

The new feature of the SLAT is that the items with at least one of the two pairs of groupings (in these examples, ones identified as "Type_") do not have the close relation of being members of a single category. Nevertheless, they may participate in more complex representational groupings. The result of this change is a new type of measure. Rather than being a measure of strengths of associations among categories (what the IAT measures), the SLAT provides a measure of relationships among representations more complex than categories—relationships that can be identified (in cognitive theory) as more complex representational structures.

The Asian stereotype SLAT (FIG. 5) differs from previous stereotype investigations involving the IAT because it makes use of a complex multi-trait stereotype (shyness, diligence, diminutiveness) rather than a single stereotypic trait. In standard IATs, an association involving one component trait of a stereotype (e.g., shyness) and a social category (such as Asian) may be assessed. The task illustrated in FIG. 5 goes beyond the standard IAT measure of stereotype by combining multiple traits into a higher-level grouping. The task of FIG. 5 should reveal an Asian American stereotype by showing faster performance when Type AA and Asian locations are assigned to the same response than when Type AA and North American locations are assigned to the same response. If the FIG. 5 illustration were altered by switching a few items between the two groupings—perhaps switching diligent with pushy and study with play (see lines 201 and 202 in FIG. 5)—the resulting item collections would not map coherently map onto any known stereotypic representation. Performance when this modified Type AA group and Asian locations are assigned to the same response should be no faster than performance when the modified Type AA group is paired with North American locations.

The final sequence of three illustrative tests (FIGS. 6-8) related to smoking show alternative ways of assessing representations that can be used in studies of smoking and health. The first of these tests (FIG. 6) uses the established IAT method of assessing associations among four categories (health, illness, cigarettes, no cigarettes). In responding to this test, many people will show an association of cigarettes with illness—an association that is likely to be stronger for non-smokers than for smokers. The SLAT in FIG. 7 may also show a difference between smokers and non-smokers. However, more interesting is the possibility that this measure will detect interesting differences among smokers. The SLAT in FIG. 8 is the only illustration here in which all four categories are of the higher-order type. The categories of cigarette and no cigarette of FIGS. 6 and 7 are replaced with Type S (503 in FIG. 8, representing smoking behavior) and Type NS (504 in FIG. 8, representing non-smoking behavior). Again, this is a test for which the most interesting uses may be in identifying important cognitive differences among smokers. These psychological differences among smokers may be predictive of the likelihood of giving up smoking. Addicted smokers who have stronger associations of smoking behavior (Type S, 503) with unhealthy behavior (Type U, 504) may be better prepared (cognitively) to abandon smoking.

The SLAT has been illustrated here exclusively with groupings of words used to identify representations more complex than the category level. These groupings can be constructed equally using visual images. For example, functional equivalents of Type H and Type U in FIGS. 7 and 8 can be composed of visual images depicting actions of the types named in those groupings.

These methods of the Second-Level Association Test create new possibilities both for theoretical investigations in psychology and for practical applications in health behavior and consumer psychology.

To further illustrate embodiments of the present invention, the following non-limiting Examples of the improved IAT are provided.

EXAMPLES

| \ | Experiment 1 | \ |
|---|---|---|
| Domain | Concepts | Attributes |
| Political Attitude | Bush vs. Kerry | Good vs. Bad |
| Gender Identity | Male vs. Female | Self vs. Other |

After a practice block in an unrelated domain, 40 student participants completed the political attitude and gender identity improved IATs in one of 16 counterbalanced sequences. Unlike the standard IAT, where effects of response key are absent, in the improved IAT subjects were faster on match trials (M=709 ms) than mismatch trials (M=770 ms), $F(1, 39)=112$, $p=5 \times 10$-13. This effect serves as a manipulation check for focal category instructions. Predicted effects emerged for gender identity and political attitude only when Good and Self were used as focal categories. The corresponding effects were negligible when Bad and Other were focal categories. The correlation between these two forms of the improved IAT did not differ significantly from zero. These trends are reflected in the table of correlations below.

| Instructions corresponding to "right key" of FIG. 2 | Correlate | Match Trials | Mismatch Trials |
|---|---|---|---|
| Good + Bush vs. Good + Kerry | Explicit | 0.75 | 0.62 |
| Bad + Kerry vs. Bad + Bush | Kerry Preference | −0.02 | 0.14 |
| Self + Male vs. Self + Female | Subject | 0.70 | 0.62 |
| Other + Female vs. Other + Male | Gender | −0.13 | 0.17 |

| Experiment 2 | | |
|---|---|---|
| Domain | Concepts | Attributes |
| Cola Attitude | Coke vs. Pepsi | Good vs. Bad |
| Ethnic Identity | Asian vs. European | Self vs. Other |

There were 155 participants in this experiment which had improved IATs for cola attitude and ethnic identity. The attitude and identity IATs used Good and Self as categories for the focal key (corresponding to the right key of FIG. 2). The spacing factor was implemented by sequences in which each improved IAT was either presented twice in a row or with the maximum possible separation. The novelty factor was implemented by sequences that either repeated the identical set of exemplars or presented novel category exemplars during the second administration. Spacing and novelty had no effect in any of the IATs. Effects of the order of presentation of the two IAT blocks were negligible. Match effects were powerful in all IATs. The implicit-explicit correlations were in the predicted direction and had values of 0.75, 0.60, 0.63, and 0.63 for gender identity, ethnic identity, political attitude, and cola attitude, respectively.

Although the above discussion discloses various exemplary embodiments of the invention, it should be apparent to those skilled in the art that variations and modifications may achieve some of the advantages of the invention without departing from the true scope of the invention. Accordingly, other embodiments are within the scope of the following claims.

What is claimed is:

1. A method of measuring a subject's strength of associations involving each of a first pair of first and second categories with each of a second pair of third and fourth categories, without any use of single-task practice trials, the method comprising:
   in a first set of trials, causing presentation, via a display device coupled to a computer accessible to a subject, of a first series of exemplars, the first series of exemplars including exemplars from all four categories;
   storing performance by the subject of a series of tasks in the first set of trials, wherein the tasks in the first set of trials are to respond in a first manner when there is presented an exemplar of either the first category or the third category and in a second manner when there is presented an exemplar in any other category, and wherein the task as to the second manner of response has no explicit reference to the second or fourth category;
   in a second set of trials, causing presentation, via the display device, of a second series of exemplars in the second set of trials, the second series of exemplars including exemplars from all four categories;
   storing performance by the subject of a series of tasks in the second set of trials, wherein the tasks in the second set of trials are to respond in a first manner when there is presented an exemplar of either the second category or the third category and in a second manner when there is presented an exemplar in any other category, and wherein the task as to the second manner of response has no explicit reference to the first or fourth category;
   measuring, in a first computer process, for each response in each trial, a time elapsed between exemplar presentation to the subject and response of the subject via the computer to the presented exemplar, to produce a latency measurement therefor; and
   in a second computer process, calculating a measure of the subject's strength of associations involving each of the first and second categories with each of the third and fourth categories from the latency measurements, so that performance data from the subject is obtained without any use of single-task practice trials.

2. A method according to claim 1, wherein the trials of each set alternate between presenting the subject with an arbitrary exemplar in one of the first pair of categories with an arbitrary exemplar in one of the second pair of categories.

3. A method according to claim 1, wherein calculating a measure includes calculating a difference between a mean latency for the first set of trials and a mean latency for the second set of trials and dividing the difference by a standard deviation of the latency measurements for the first and the second set of trials.

4. A method according to claim 1, wherein the subject is presented with fewer than 100 trials.

5. A method according to claim 1, wherein the subject is presented with fewer than 50 trials.

6. A method according to claim 1, wherein the first pair of categories includes an attribute and an opposing attribute.

7. A method according to claim 1, wherein the first pair of categories includes a pleasant valence category and an opposed unpleasant valence category, and the method measures the subject's strength of associations involving attitude.

8. A method according to claim 1, wherein the first pair of categories includes human group categories and the second pair of categories includes trait categories, and the method measures the subject's strength of associations involving stereotypes.

9. A method according to claim 1, wherein the first pair of categories includes a self-referring category and an other-referring category, and the method measures the subject's strength of associations involving identity.

10. A method according to claim 1, further comprising:
    repeating the first set of trials with a third series of exemplars; and
    repeating the second set of trials with a fourth series of exemplars.

11. A method according to claim 10, wherein the subject is not required to respond to any trials other than those trials recited.

12. A method according to claim 1, wherein the subject is not required to respond to any trials other than those trials recited.

13. A method according to claim 1, wherein measuring latency in each trial includes measuring from the time of exemplar presentation to the subject to a correct response by the subject.

* * * * *